Aug. 11, 1953 L. L. FRYE Plant Pat. 1,210
PEACH TREE
Filed Sept. 12, 1952
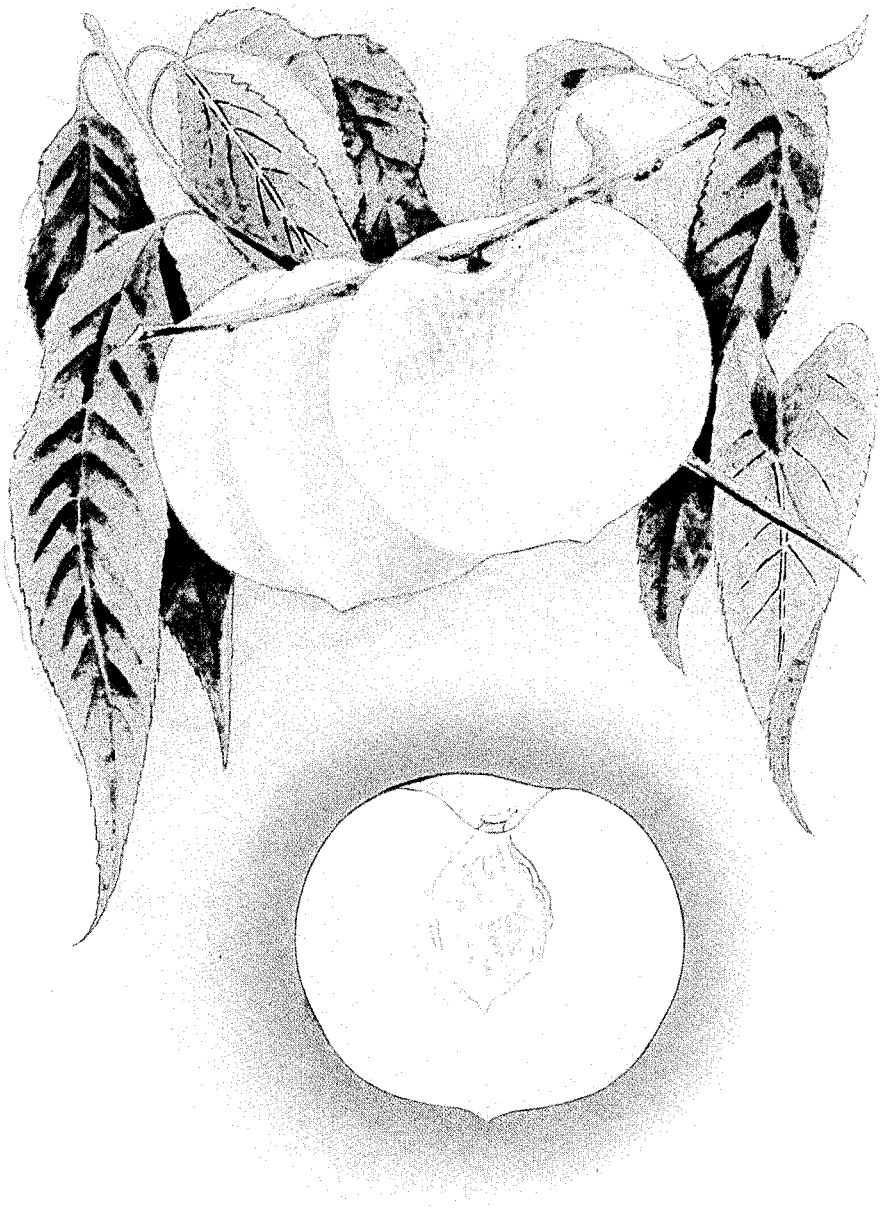
WITNESS
Addison J. Avery
INVENTOR
LLOYD LOUIS FRYE
Webster & Webster
ATTYS.

Patented Aug. 11, 1953 Plant Pat. 1,210

UNITED STATES PATENT OFFICE 1,210

PEACH TREE

Lloyd Louis Frye, Yuba City, Calif.

Application September 12, 1952, Serial No. 309,391

1 Claim. (Cl. 47—62)

The present invention is directed to a new and distinct variety of peach tree which bears large to medium sized, yellow-fleshed, clingstone fruit; the principal distinguishing characteristic of the present variety being an early ripening period of the fruit relative to the well known Paloro peach with which it otherwise has close resemblance.

The present variety originated, and was brought into propagation by me, in the following manner:

As a licensed nurseryman interested in the sundry varieties of fruit, especially peaches, grown in the State of California, it has been my practice to conduct a continuing examination of orchard trees, particularly those in orchards under my care or supervision.

In the course of such activity I make careful comparisons between the tree and fruit characteristics of different peach varieties, and as a result of such activity the present variety—as a sport of the well-known Paloro (unpatented) peach variety—was brought forward by me as being of especial promise for commercial canning of the fruit. The present variety of peach tree was discovered by me in an orchard on my family ranch located near Yuba City, California, on which ranch I was a resident at the time of discovery, and which orchard I then operated and now continue to operate.

The instant variety of peach tree has subsequently been asexually reproduced by budding onto mature root stock in an orchard near Yuba City, California, and the reproductions have been found to carry forward all of the novel characteristics of the parent.

In the drawings:

Fig. 1 is a perspective view of fruit of the present variety, together with stems and leaves.

Fig. 2 is a sectional view taken axially of the fruit, with the cling-stone partially exposed.

Referring now more particularly to the pomological details of the new and distinct variety of peach tree, the following is an outline description thereof; all major color plate identifications being by reference to Maerz and Paul Dictionary of Color.

Tree: Medium size; vigorous; upright—spreading; dense; vase formed; productive; regular bearer.

Trunk: Medium size; medium texture.

Branches: Medium size. Current growth smooth, green; reddish where exposed; one year old wood greenish brown to brown, smooth to medium.

*Lenticels.*—Medium number; medium size.

Leaves: Medium size. Average length, 6¼″ to 6½″; average width, 1⅜″ to $1\frac{9}{16}$″, mostly 1½″. Ovate—lanceolate; medium thick; smooth.

*Apex.*—Acutely pointed.

*Base.*—Acuminate.

*Color.*—Medium green on top side (22–L–6); lighter green on under side (22–K–4).

*Margin.*—Finely serrate.

*Petiole.*—Medium to short in length; thick to medium.

*Glands.*—Eglandular.

*Stipules.*—Dehiscent.

Flower buds: Large to medium size; medium length; obtuse; appressed; pubescent.

Flowers: Dates of first and full bloom—medium as compared with other varieties; March 8, 1952, and March 18, 1952, respectively.

*Size.*—Small—non-showy.

*Color.*—Salmon.

Fruit: Maturity when described—eating—ripe. Date—July 23, 1952 (all fruit on tree full ripe for canning purposes).

*Size.*—Uniform; large to medium. Average diameter axially, $2\frac{7}{16}$″ to 2⅞″; average transverse in suture plane, $2\frac{13}{16}$″ to 3¼″.

*Form.*—Uniform; symmetrical; oblatish—round; very slightly compressed laterally.

*Suture.*—Distinct; shallow; extends from base to apex, with slight depression beyond pistil point.

*Ventral surface.*—Rounded slightly; lipped throughout both sides; lips equal, or with one slightly larger.

*Cavity.*—Narrow; flaring; abrupt; elongated in suture plane with suture showing on one side. Average depth, $\frac{9}{16}$″ to $\frac{11}{16}$″; average breadth, ½″.

*Base.*—Rounded to truncate.

*Apex.*—Rounded to truncate; depressed along suture.

*Pistil point.*—Apical.

Skin: Medium thick; medium tough; tenaceous to flesh.

*Tendency to crack.*—None.

*Down.*—Abundant; medium length.

*Color.*—Yellow (9–L–3) to golden yellow (9–K–8), with a medium red blush (3–L–3) on the sunny side, washed occasionally or obscurely mottled with a dark red (5–L–6).

Flesh:

*Color.*—Yellow (9–L–5) mottled with red next to stone throughout, but not penetrating the flesh.

*Amygalin.*—Scant or wanting.

*Juice.*—Moderate.
*Texture.*—Non-melting; firm; fine; meaty.
*Fibers.*—Few; tender.
*Ripens.*—Evenly.
*Flavor.*—Mild.
*Aroma.*—Slight.
*Eating quality.*—Fair—a canning clingstone.

Stone: Cling; adheres to flesh over entire surface.

*Size.*—Medium. Average length, $1\frac{3}{16}''$ to $1\frac{3}{8}''$; average breadth, $\frac{15}{16}''$ to $1\frac{1}{8}''$; average thickness, $\frac{3}{4}''$ to $\frac{7}{8}''$.
*Form.*—Round—ovate.
*Base.*—Slightly oblique toward the ventral suture.
*Hilum.*—Oval.
*Apex.*—Rounded with short sharp tip.
*Sides.*—Nearly equal.
*Surface.*—Irregularly furrowed throughout.
*Ridges.*—Rounded.
*Dorsal edge.*—Full, with shallow narrow groove.
*Ridges.*—On either side.
*Tendency to split.*—Slight.

*Color.*—Reddish brown (5–E–11).

Use: Canning.

Keeping quality: Medium.

The instant variety of peach tree is comparable to the well known Paloro variety in general fruit and tree characteristics, but ripens for canning use approximately twelve days earlier than the fruit of the Paloro peach trees (unpatented) growing in comparable situations; all fruit of trees of the present variety full-ripening for canning at approximately the same time.

The tree and its fruit herein described may vary in slight detail due to climatic and soil conditions under which the variety may be grown.

Having thus described my invention, I claim:

A new and distinct variety of peach tree substantially as described and illustrated, characterized by its general similarity in tree and fruit with the Paloro peach but dominantly distinguished therefrom by a ripening period substantially twelve days earlier.

LLOYD LOUIS FRYE.

No references cited.